United States Patent [19]

Fogel

[11] Patent Number: 4,459,180
[45] Date of Patent: Jul. 10, 1984

[54] METHOD AND MEANS FOR COMPENSATING FOR IR VOLTAGE DROP IN ELECTROCHEMICAL CELLS

[75] Inventor: John D. Fogel, Schwenksville, Pa.

[73] Assignee: General Signal Corporation, Stamford, Conn.

[21] Appl. No.: 495,322

[22] Filed: May 16, 1983

[51] Int. Cl.³ .............................................. G01N 27/46
[52] U.S. Cl. .................................... 204/1 T; 73/1 G; 204/412; 204/415; 204/406; 364/571
[58] Field of Search ............. 204/400, 401, 406, 415, 204/412, 1 P, 1 T; 73/1 G; 364/571

[56] References Cited

U.S. PATENT DOCUMENTS

| | | | |
|---|---|---|---|
| 3,260,656 | 7/1966 | Ross, Jr. .................................. | 204/195 |
| 4,042,465 | 8/1977 | Morong et al. .................. | 204/406 X |
| 4,076,596 | 2/1978 | Connery et al. ..................... | 204/1 T |
| 4,167,163 | 9/1979 | Möder ............................. | 204/401 X |
| 4,207,146 | 6/1980 | Kunke .............................. | 204/406 X |
| 4,269,684 | 5/1981 | Zick ....................................... | 204/406 |
| 4,321,113 | 3/1982 | Grambow et al. ............. | 204/406 X |
| 4,366,039 | 12/1982 | Uchida et al. ..................... | 204/406 |

Primary Examiner—G. L. Kaplan
Assistant Examiner—Nam X. Nguyen
Attorney, Agent, or Firm—William G. Miller, Jr.; Harold Huberfeld

[57] ABSTRACT

Apparatus for compensating for the IR drop in a polarographic type electrochemical cell which utilizes an injected current for in situ calibration includes means operable for a brief period of the current injection to change the cell bias so as to maintain the total cell current for that period at the value existing prior to current injection as well as means for maintaining throughout the remainder of the injection period the cell bias which exists at the end of the brief period.

3 Claims, 20 Drawing Figures

METHOD AND MEANS FOR COMPENSATING FOR IR VOLTAGE DROP IN ELECTROCHEMICAL CELLS

CROSS REFERENCE TO RELATED PATENT APPLICATION

A U.S. patent application Ser. No. 495,302 concurrently filed with the present application in the names of Robert M. Taylor and William C. Wiley claims certain of the subject matter disclosed but not claimed herein.

BACKGROUND OF THE INVENTION

This invention relates to a method and apparatus for compensating for the IR drop which can occur between electrodes in an electrochemical cell when it is subjected to a current field other than that which results from the measurement process alone. This invention is particularly useful in compensating for the IR drop which occurs when an electrochemical cell is recalibrated by the brief application of a d.c. current to a supplementary electrode as set forth in a U.S. patent application Ser. No. 495,302 filed on the same date as this application described below.

The description of the electrochemical cells disclosed in U.S. Pat. No. 4,076,596 is hereby incorporated by reference.

As set forth in the last mentioned U.S. patent, the basic polarographic apparatus as improved by Clark is described in U.S. Pat. No. 2,013,386 and is known as the Clark cell. The Clark cell utilizes a dual electrode structure immersed in an electrolyte and encased in a membrane which is permeable to the species to be measured. Typically, when used for oxygen analysis the cathode in the Clark cell is formed of platinum or gold and is located closely adjacent to the membrane while the anode is formed of silver or lead, with an electrolyte usually made of an aqueous alkaline halide solution. In operation, the Clark cells is characterized by the fact that the cell consumes the species being measured and therefore causes a depletion of the species from the fluid sample in which the cell is immersed.

To avoid disadvantages such as stirring dependencies, a cell structure of the type shown in U.S. Pat. No. 3,260,656 was proposed by Ross. That cell utilized an electrode system which consumed the species being measured at one electrode which generated a like quantity of the species at the electrode of opposite polarity. The electrodes were closely spaced so as to avoid depletion of the species from the sample.

The Ross type cell was further improved by the Connery et al cell structure of U.S. Pat. No. 4,076,596. For the purpose of this description, those cells which characteristically deplete the sample of the species being measured are referred to as Clark-type cells, or cells which operate in the Clark mode, whereas those cells which do not deplete the sample, such as the Ross or Connery et al. cells, are herein referred to generically as the Ross-type cells or cells operating in the Ross mode.

Electrochemical cells of the Ross type as described in U.S. Pat. No. 4,076,596 have been found to be very useful in applications where it is necessary to sterilize the cell before it is used in order to prevent contamination of the sample to be measured. In such applications and in others, it is not possible for the cell must be withdrawn from the sample and inserted into a known but possibly contaminated standard sample for recalibration. During the course of normal use these cells require recalibration because of the normal cell drift which takes place.

In the related application referenced above, certain coworkers of mine have disclosed a method for recalibrating electrochemical cells of the Ross type in situ, by applying a d.c. current to a supplementary electrode in the cell and measuring the change in cathode current which results. That change is then related to the change which occurred under similar conditions at the time of a previous or initial calibration as an indication of the change in calibration which has occurred.

This method of recalibration has the disadvantage that it creates certain small errors as a result of the additional current introduced into the cell. These errors are due to an interelectrode IR drop which results from that additional current, and manual adjustment of the bias for the cell electrode to compensate for those errors is a tedious and time consuming procedure.

It is an object of this invention to provide a method and apparatus for automatically compensating for the IR drop introduced by recalibration or by other sources of additional current in the cell.

SUMMARY OF THE INVENTION

There is provided apparatus for compensating for the IR drop produced in polarographic type cells by currents in the cells which are other than the current used for measuring purposes. Such currents may, for example, be injected into the cell as part of a procedure for recalibration, in situ. To compensate for the IR drop in the cell due to such currents, there is provided a means which is operable for a brief initial part of the current injection period for constantly changing the cell bias so as to maintain the total cell current constant for that part of the period. The duration of that part of the period must be at least that which is necessary to establish the new bias required to compensate for the IR drop but that part of the period should not be sufficient to extend into the portion of the injection period when electrochemical action due to the injection affects the total cell current. There is also provided means for maintaining throughout the injection period that cell bias which exists just prior to the end of the brief part of the injection period when the cell current is clamped as described above. This adjusted bias compensates for the IR drop due to injected current so that the recalibration is not affected by the IR drop.

BRIEF DESCRIPTION OF THE DRAWINGS

In the drawings, in which like reference characters refer to like elements.

DESCRIPTION OF THE PREFERRED EMBODIMENT

The calibration of chemical analyzers usually involves adjusting the measuring instrument to provide a correct reading for the sample being analyzed, with the particular cell being used for the measurement, and under the existing ambient conditions. The measuring instrument is adjusted to the sensitivity of the cell as determined by the calibration procedure. For the purposes of this description, the process of determining the sensitivity of the cell shall be considered as the process of calibrating or recalibrating the cell as contrasted with the adjustment of the instrument in its calibration or recalibration. Thus, in an analyzer for a particular species, the sensitivity, S, may be considered as the species concentration, C, of the sample divided by the measured cathode current, $I_c$, as determined by the measuring instrument. Thus, $$S = (C/I_c) \qquad (1)$$

For the purposes of the subsequent description, it will be assumed that the species to be measured is oxygen although those skilled in the art will understand that with appropriate changes in electrode bias and electrode polarity other species, such as hydrogen, can be measured; and the associated cells can be recalibrated in accordance with this invention.

Figure 1:
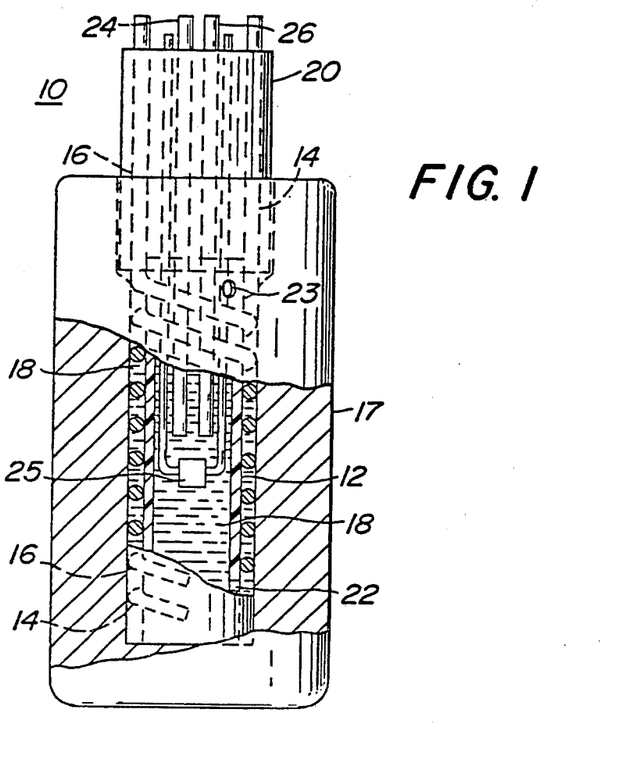
FIG. 1 is a front elevation, partially in cross-section, of a polarographic cell of the type with which the present invention is concerned.

In FIG. 1, which is very similar to the construction of FIG. 7 of U.S. Pat. No. 4,076,596, there is shown an electrochemical cell 10, such as an oxygen cell, with which this invention is useful. This cell comprises a hollow cylindrical base 12 of insulating material which has wound on its surface interleaved wire electrodes forming spirals about the base. These electrodes are shown as wires 14 and 16. The surfaces of these electrodes are exposed to the electrolyte 18 which is contained both in the internal portion of the cylindrical base as well as in that area between the electrodes exterior to the cylindrical base. The spacing between the electrodes 14 and 16 as they spiral around the base 12 is sufficiently close with respect to the thickness of the membrane 17 which covers the spiral winding so that there will be no depletion of the oxygen from the sample in which the cell is immersed, but instead the oxygen will be generated at one electrode and consumed at the other electrode in a quantity dependent of the concentration of the oxygen in the sample being measured.

The electrodes are brought out of the cell through a body portion 20 to which the membrane 17 is closely fitted so as to retain the electrolyte 18 in the spaces between the electrodes and in the interior portion of the base. There will be, of course, a thin film of electrolyte between the membrane 17 and the electrodes 14 and 16.

As shown in FIG. 1, two holes are provided in the base 12. They are shown as the lower hole or aperture 22, and the upper hole 23. These holes are provided so that the electrolyte interior to the base is in communication with the electrolyte exterior to the base. Also, as shown in FIG. 1, two additional electrodes, 24 and 26, enter through the body portion 20 directly into the interior of the cylindrical base 12 so that they are immersed in the electrolyte contained therein. Electrode 24 may be considered the reference electrode and electrode 26 will be denominated the fourth electrode.

The sensitivity or calibration factor of the cell is determined by a number of factors such as Henry's Law, sensor geometry (electrode area, spacing, membrane tightness), $O_2$ diffusion rates (which are temperature dependent) in both electrolyte solution and membrane materials, electrode surface activity (effective active surface vs. geometric surface), electrolyte composition, drift in reference electrode potential, and electronic drift in the bias voltage applied to the cell. Some of these factors, such as temperature, can be compensated automatically, but others, such as the active area of the electrode, must be accounted for initially by calibration in a known sample with periodic recalibration.

The automatic recalibration in situ provided by the present invention utilizes the fourth electrode 26 to inject a transient such as a pulse of additional electrical current into the cell. This injection is made so that the fourth electrode acts as a second cathode for a short period of time, such as three seconds.

In response to a stepwise change in the current in the fourth electrode, the anode current will also increase accordingly. This is true since the anode current must at all times equal the total cathode current. Thus, where:

$I_a$ is the anode current
$I_c$ is the total cathode current
$I'_c$ is the normal cathode current when fourth electrode is not activated
$I_4$ is the fourth electrode current $$I_a = I_c \qquad (2)$$

$$I_c = I'_c + I_4 \qquad (3)$$

To accomplish the increase in anode current, the anode must electrolyze more water from the electrolyte and produce, thereby, more oxygen. The additional oxygen diffuses to the cathode where it is reduced, causing the total cathode current, $I_c$, to increase. Applicants use the rate of increase in $I_c$, which will hereafter be referred to as the transient response Δ, to provide an indication of the sensitivity of the cell at the time of activation of the fourth electrode. If a similar determination of Δ is made at the time when the cell is initially calibrated using a known sample, it is then possible to make the subsequent recalibration by modifying the cell sensitivity, $S_1$, determined at initial calibration, in accordance with the change in cell sensitivity.

Figure 2:
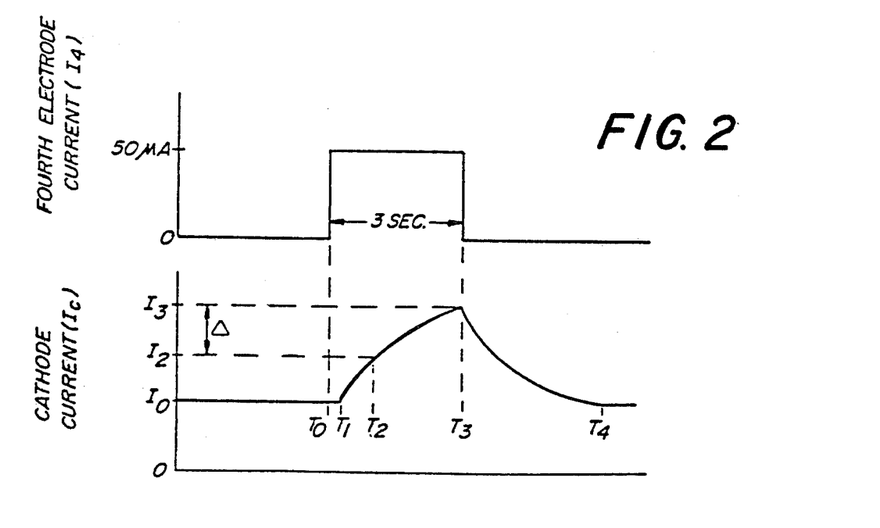
FIG. 2 is a graphical representation of both the fourth electrode current and the cathode current, showing their relationship.

FIG. 2 illustrates the step change in the fourth electrode current which is initiated to determine the transient response, $\Delta$, and the resulting change in $I_c$ during activation of the fourth electrode. Prior to time $T_o$ the fourth electrode is off and the cathode current measured by the measuring instrument is $I_o$. Again, assuming that an oxygen analyzer is involved, $I_o$ is related to $O_2$ concentration.

At $T_o$ the fourth electrode is activated by a constant current source which must provide a current sufficient to cause a change in $I_c$ which exceeds the noise in the $I_c$ signal. The current source is shown as providing 50 $\mu$A of current. That current continues to flow through the fourth electrode for a 3 second interval as shown in FIG. 2.

At $T_1$, a very short interval later, the additional oxygen produced by the anode 16 begins to arrive at the cathode 14 causing $I_c$ to begin to increase.

At later times, $T_2$ and $T_3$ (typically 1 and 3 seconds after $T_0$), the cathode current is sampled and the difference between those two currents, $\Delta$, is determined.

After $T_3$ the fourth electrode is deactivated and $I_c$ begins to decay back to $I_o$, which it reaches at a later time, $T_4$.

Alternatively, the value of the transient response $\Delta$, the quantity indicative of the cell's sensitivity to a current injection, can be determined by measuring the slope of the curve $I_c$ between $T_2$ and $T_3$ or by measuring the slope of the decay after $T_3$. It is, of course, also possible to arrive at a value for $\Delta$ by measuring the area under the curve $I_c$, since the area under the curve would be related to the rate of change of $I_c$ during a particular interval.

It is possible to operate the fourth electrode as an anode instead of as a cathode. That would cause the normal anodic current to decrease, and consequently cause the oxygen produced at the normal anode to decrease. The subsequent rate of decrease in the cathode current $I_c$, as the cathode experiences a change in oxygen concentration in the electrolyte, can be used as a measure of sensitivity in a manner analogous to that described above.

To perform a recalibration of the cell without using a known sample, the value of $\Delta$ at the time of recalibration is compared to the value of $\Delta$ at the time of a previous or initial calibration. The comparison between the values of $\Delta$ can be expressed in accordance with the ratio of the two values or the difference between the two values.

Since both the cathode current, $I_c$, and the value of $\Delta$ are temperature sensitive, it is necessary to introduce temperature compensation into the calculation of the cell sensitivity on recalibration. Thus, using the ratio of the values of $\Delta$ as the factor by which the sensitivity has changed, the sensitivity of the cell at recalibration can be calculated by the following equation:

$$S_2 = S_1 \times \exp\left[B_1\left(\frac{T_2 - T_1}{T_2 T_1}\right)\right] \times \Delta_1/\Delta_2 \times \exp\left[B_2\left(\frac{T_1 - T_2}{T_2 T_1}\right)\right] \quad (4)$$

where $S_2$ = sensitivity of cell at recalibration
$S_1$ = sensitivity of cell at initial calibration
$\Delta_1$ = value of $\Delta$ measured during initial calibration
$\Delta_2$ = value of $\Delta$ measured during recalibration
$T_1$ = temperature (°K.) at initial calibration
$T_2$ = temperature (°K.) at recalibration
$B_1$ = cathode current temperature coefficient
$B_2$ = temperature coefficient of $\Delta$.

The temperature measurements required to solve the above equation are obtained from the thermistor 25 shown in FIG. 1 as being incorporated as part of the cell so that it measures the electrolyte temperature. A thermistor or another temperature sensitive element may be a completely separate element immersed in the sample being measured.

Recalibration by the injection of an additional current into the cell, as described above, requires adjustment to the cell bias as a compensation for the effect of the IR drop which appears between the reference electrode and the cathode as a result of the added current from the fourth electrode. This compensation is required when the structure of the cell causes the potential measuring path between the cathode and the reference electrode to be in the current field created between the fourth electrode and the anode by the current injection at the fourth electrode.

The cell bias as represented by the potential at the reference electrode (assuming a grounded cathode) is preferably maintained constant, for example, in the 0.6 to 0.7 volt region when using a silver/silver chloride reference electrode. For accurate measurement it is necessary to control the anode voltage to maintain the cathode potential at the same part of its characteristic at all times so that the cathode current is a true measure of oxygen concentration. When current is injected into the cell at the fourth electrode, the reference-to-cathode potential is caused to shift so that the cathode goes from the region of the cell characteristic known as the oxygen wave toward the region known as the hydrogen wave, thus causing increase of the cathode current.

The compensation for the IR drop due to the current injection made during recalibration can be accomplished by first adjusting the cell bias so as to clamp the cathode current at the value it had before the current injection and then after a brief initial part (200 milliseconds, for example) of the injection period holding the bias voltage at its corrected value, which will be its existing value at the end of the brief part of the period. The bias voltage is maintained at its corrected value until the current injection has ended. The brief period should be at least long enough to permit adjustment of the cell bias to accomplish the IR compensation but not so long that it includes any part of the injection period when the electrochemical effects of the injected current are going to affect the total cell current.

Figure 3:
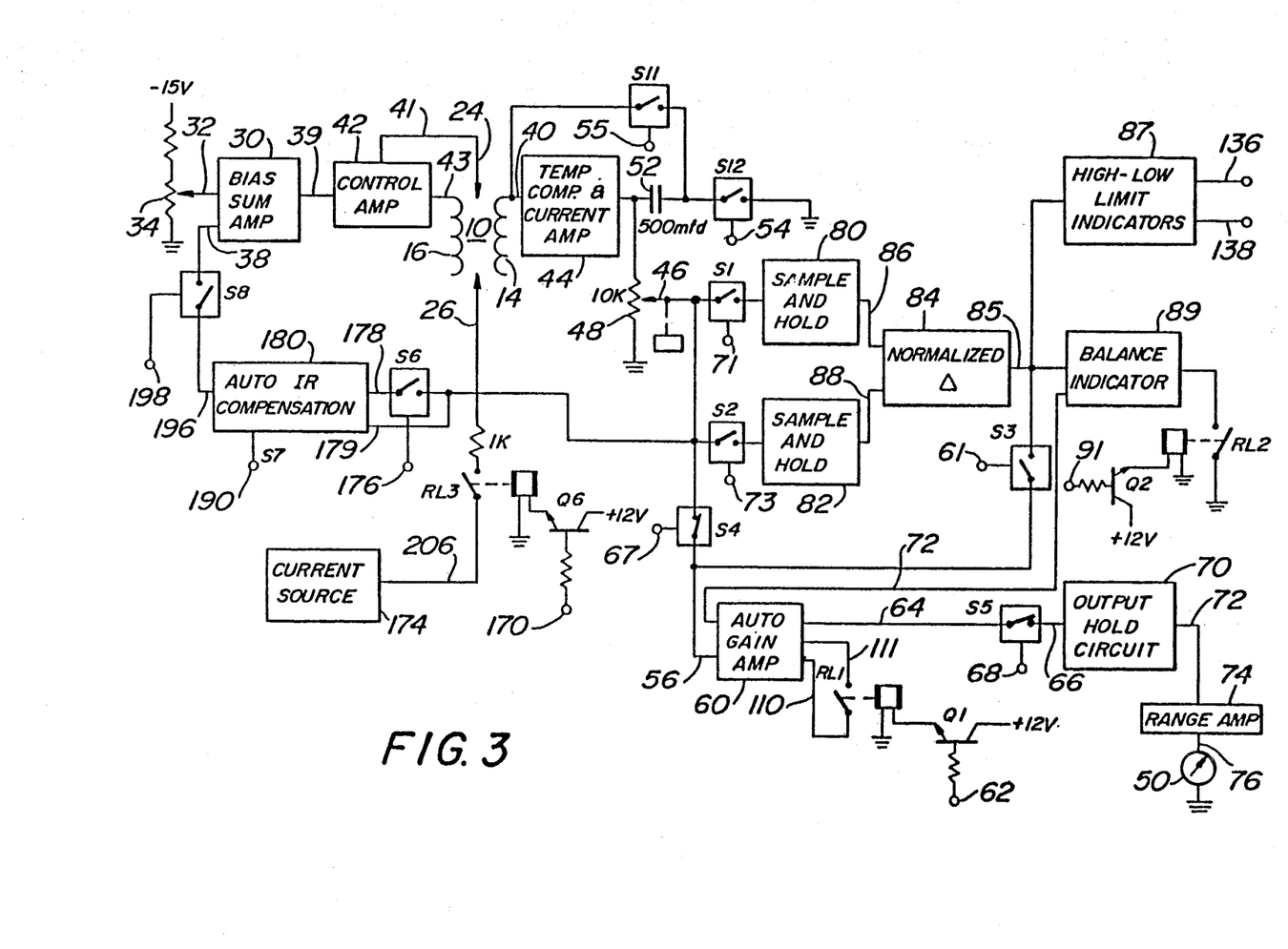
FIG. 3 is a block diagram showing an analog circuit for carrying out the invention.

Apparatus for providing automatic calibration in situ is shown in FIG. 3 where the cell 10 is shown diagramatically with its cathodes 14, anode 16, reference electrode 24, and a fourth electrode 26.

Calibration can advantageously be carried out on a periodic basis, for example once an hour. Thus, the apparatus of FIG. 3 normally operates in a measurement mode and is switched to operate in a calibration mode once each hour. Alternatively the calibration may be carried out on demand of the operator.

A bias summing amplifier circuit 30 is provided to determine the bias which results by control of the anode 16. This bias will have a magnitude equal to the sum of a fixed bias, determined by the position of the tap 32 on potentiometer 34 and a variable compensating bias supplied to the summing amplifier 30 on line 38. The nature of the compensating bias will be described fully in a subsequent description of the automatic IR compensation circuit of FIG. 3.

The output of the bias summing amplifier circuit 30 provides an input over line 39 to the control amplifier 42 whose function is to keep the reference electrode 24 at a predetermined potential with respect to ground, thus establishing the bias of the reference electrode 24 with respect to the cathode which nominally operates at ground. The operation of the control amplifier is such that it controls the current flow on line 43 which establishes the anode to cathode current through the sample being tested by the cell. That current is controlled at the value required in order to keep the line 41 and hence reference electrode 24 at its desired bias. This bias may, for example, be 0.7 volts or 0.6 volts as desired when the cell is being used to measure dissolved oxygen.

In the normal operation of the cell 10 for the measurement of dissolved oxygen, for example, the current amplifier and temperature compensating network 44 is provided to produce a current through potentiometer 48 proportional to the concentration of oxygen in the sample. This current produces at the tap 46 of the manually adjusted calibrating potentiometer 48 a voltage proportional to the amount of dissolved oxygen in the sample being tested. This voltage is then measured by the meter 50 through the operation of the intervening circuitry which is designed to also carry out the automatic calibration in situ of the cell 10.

The output of the current amplifier and temperature compensating network 44 is connected through capacitor 52 and normally open switch S12 to ground. This circuit in conjunction with switch S11 provides a means for suppressing spikes which may occur as a transient phenomenon due to the switching carried out in the process of automatic calibration as described below. It will be evident that switch S11 serves to connect capacitor 52 across current amplifier 44 so that the capacitor can absorb the transients.

Figure 4:
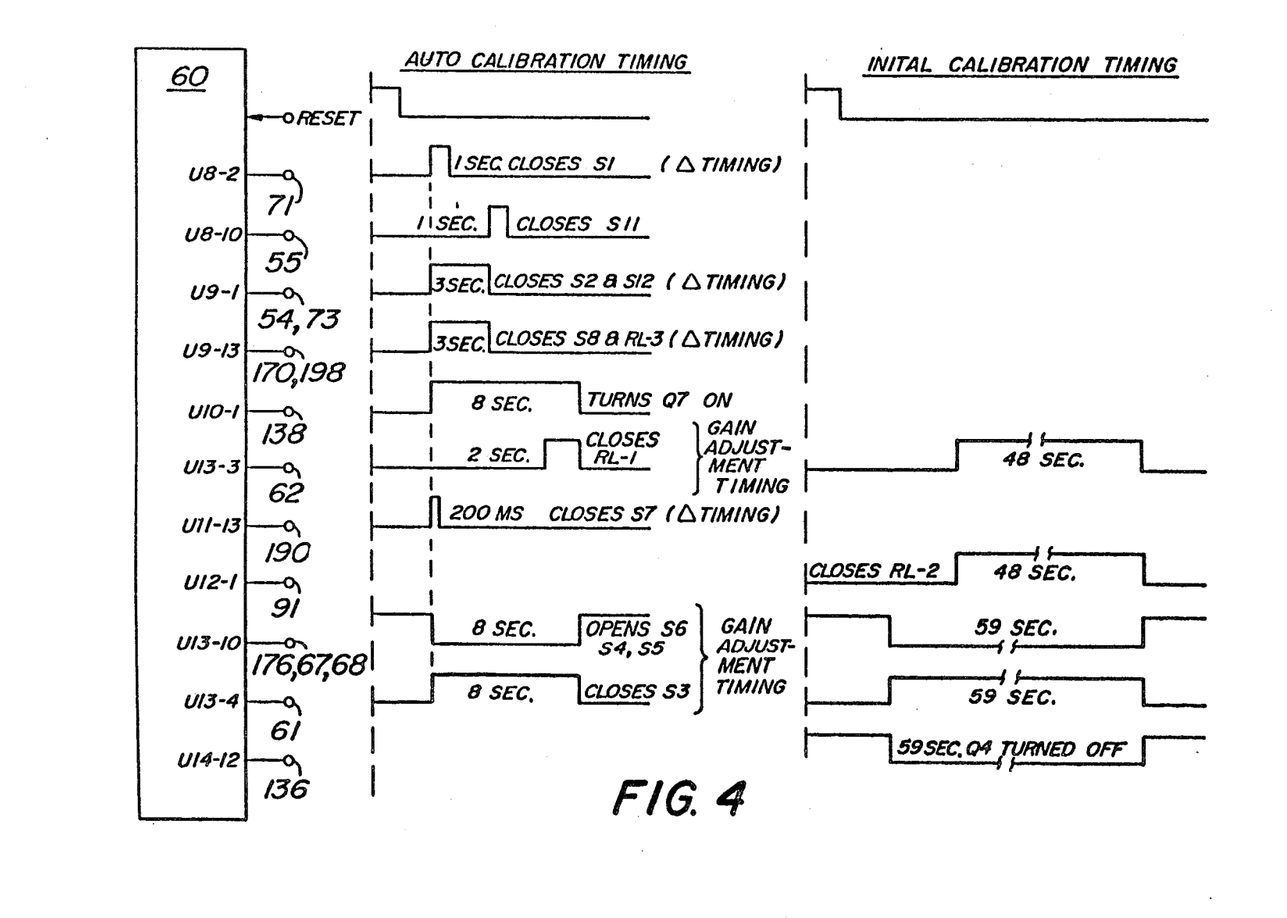
FIG. 4 is a block representation of the clock source and the timing circuits required for operation of the circuit of FIG. 3 along with a graphical representation of the timing signals produced.

The switch S12 will be closed by a timing signal supplied on terminal 54. As shown in the diagram, each of the switches, as well as the relay operating circuits, has a terminal which receives a timing signal. These timing signal inputs are identified similarly in all cases in the figures. The timing signals themselves are shown in FIG. 4. The pulses used for the periodic automatic calibration alone are so identified. They include both $\Delta$ timing signals and gain adjustment timing which handle those respective functions. Also, some of the timing signals are lengthened after a manual to automatic switch transition or a reset command from the switch of FIG. 5. These lengthened pulses are identified as relating to initial calibration timing.

Figure 4A:
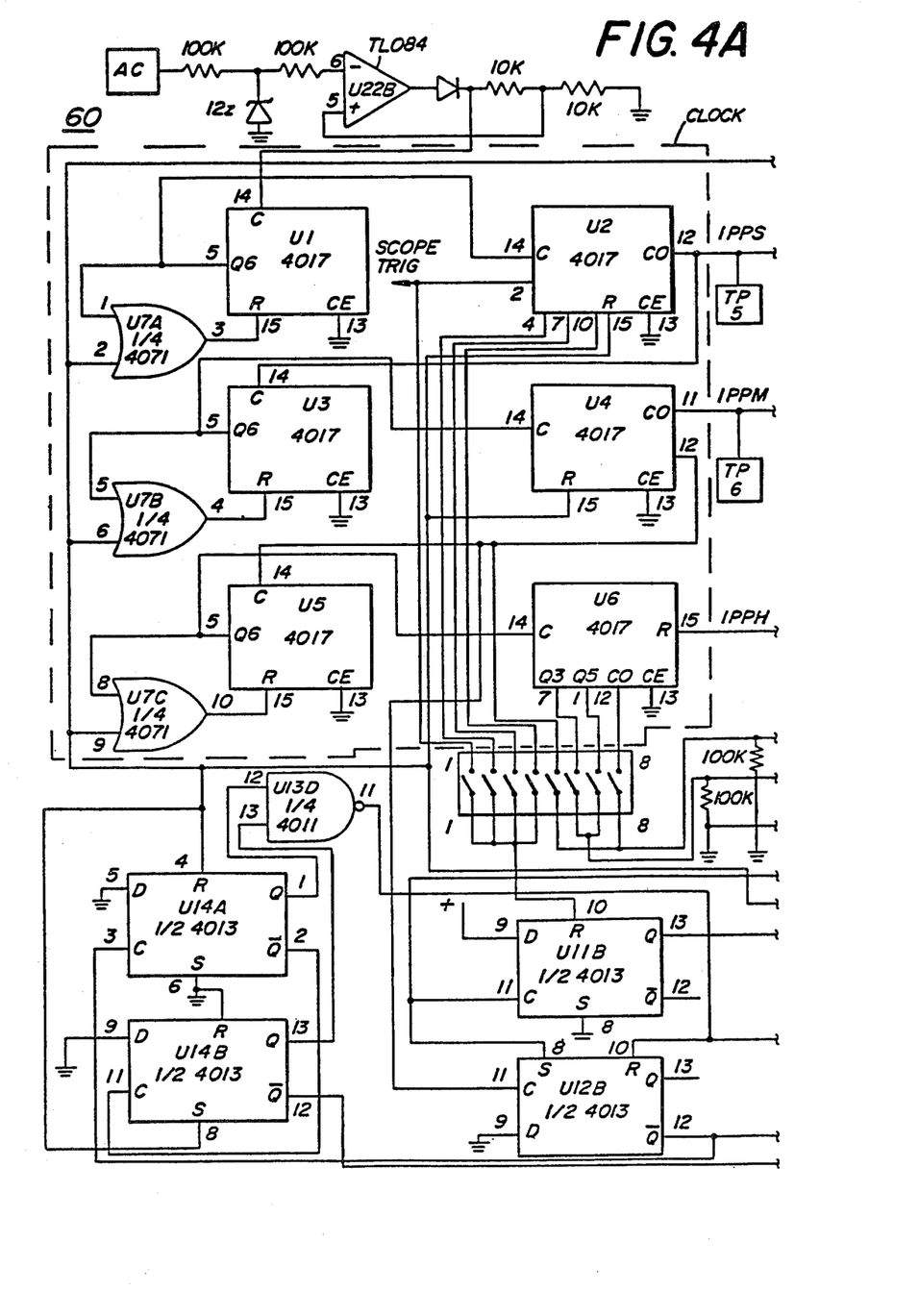
FIG. 4A is a circuit diagram of one part of the timing circuit of FIG. 4.

In FIG. 4A the enclosed block shows the six decade counter-dividers 4017 that make up the clock circuit. FIG. 4A also includes four D type flip-flops which are required to supply the 200 microsecond pulse and a 59 sec. pulse. Also, FIG. 4A includes a switch which makes possible a choice of the frequency of the automatic calibration.

Figure 4B:
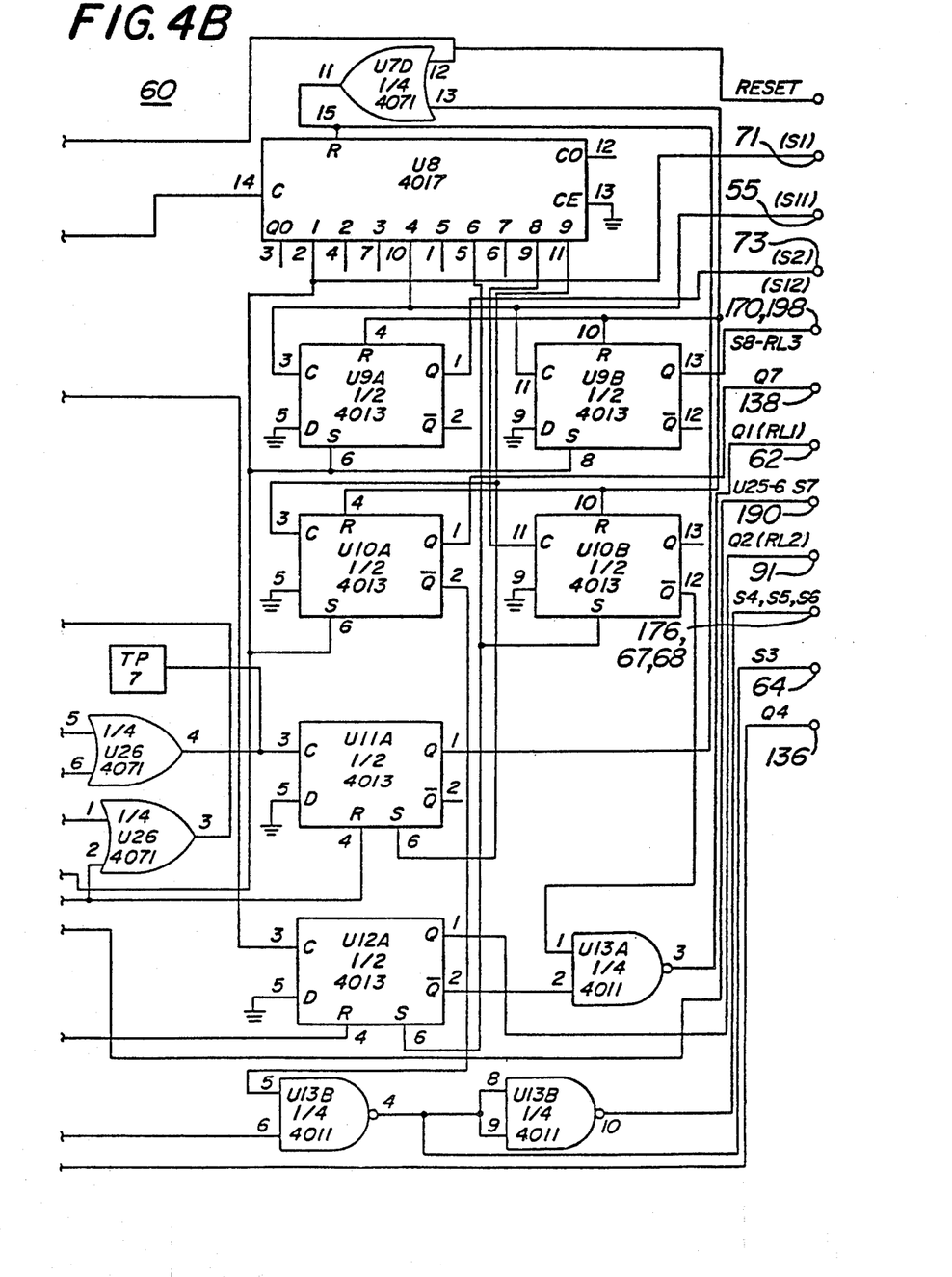
FIG. 4B is a circuit diagram of the remaining part of the timing circuit of FIG. 4.

In FIG. 4B the single counter-divider 4017 receives one pulse per second from the clock circuit of FIG. 4A and from that pulse produces the short pulses required for the automatic calibration. The six 4013 flip-flops in FIG. 4B are utilized to produce the remaining pulses.

In FIG. 4B it will be noted that the signal out of U11-1 is the once per hour resetting pulse which initiates the periodic automatic calibration.

As shown in FIG. 4 which is a diagrammatic representation of the outputs of the clock and timing circuits 60, the switch S12 will be closed for 3 seconds after the reset signal. After the circuits have been reset, the basic timing of the automatic calibration circuits in this example will be considered to consist of an 8 second period during which the calibration is completed. The calibration includes among other things a 3 second application of a constant current in the fourth electrode 26, illustrated in FIG. 2 as the time between $T_o$ and $T_3$.

The switch S4 is normally closed during the measuring period to connect the potential of tap 46 to the input line 56 of the auto gain amplifier circuit 60. That amplifier circuit has a gain which is adjustable when relay RL-1 is closed by a timing signal at terminal 62 to make transistor Q1 conductive. The closure of RL-1 by a timing signal occurs only during the calibration period. Thus, RL-1 is closed during the 2 second interval shown in FIG. 4.

The output of the amplifier circuit 60 on line 64 is conducted through normally closed switch S5 to input line 66 of the output hold circuit 70. Switch S5 is opened by a timing signal to terminal 68 which occurs when the calibration period is initiated. As shown in FIG. 4, S5 is open for the full 8 seconds of the calibration period so that the gain change effected in amplifier circuit 60 during calibration will not affect the reading of meter 50 until after calibration is complete.

The signal on line 66 which is an input to the output hold circuit 70 is used to charge a capacitor in that circuit so that the output from that circuit on line 72 will be maintained during the calibration period when S5 is open.

As shown in FIG. 3, the signal on line 72 supplies the input to the range amplifier 74 which merely establishes the necessary proportional relationship between its output on line 76 and its input as necessary for the range concentration being measured.

The various switches of FIG. 3 are operated in accordance with the timing shown in FIG. 4 to modify the circuit of FIG. 3 for the calibration period, as described below.

As shown from the timing diagrams in FIG. 4, the switches S1 and S2 are simultaneously closed by timing signals to terminals 71 and 73 with S1 remaining closed for 1 second and S2 for 3 seconds during the 8 second calibration period. S1 thus provides to the sample and hold circuit 80, until the time when it is opened at $T_2$ in the diagram of FIG. 2, a potential proportional to the cathode current. Thus, the output on line 86 will be the cathode current at $T_2$. The switch S2 provides in the output line 88 of the sample and hold circuit 82 a potential proportional to the cathode current at time $T_3$, as shown in the diagram of FIG. 2. The difference in the values from the sample and hold circuit outputs 86 and 88 represents $\Delta$ and is calculated by the circuit of block 84.

The output of the $\Delta$ circuit 84 is then supplied to the high-low limit indicators 87 and to the balance indicators 89 which is used during initialization as will be explained. The balance indicator 89 is connected in the circuit by the relay RL-2 which is energized upon receipt of a time signal at terminal 91, which is shown in FIG. 4 as being supplied for a period of 48 seconds. The output of the $\Delta$ circuit 84 also is supplied by way of switch S3, which is closed by a timing signal to terminal 61, to one of the inputs 56 of the auto gain amplifier 60. It will be noted from FIG. 4 that the switch S3 is closed for the 8 second calibration period. During that 8 second period the switches S4 and S5 are opened by timing signals to terminals 67 and 68 to prevent the normal operation of the circuit as a measuring circuit. There is also provided the necessary interconnection between the auto gain amplifier 60 and the balance indicator 89, shown by line 72 which will be explained further in a subsequent description of the circuitry.

FIGS. 3A-3K show circuits which can be used for the various blocks of FIG. 3. These circuits are described in detail below.

Figures 3A, 3B:
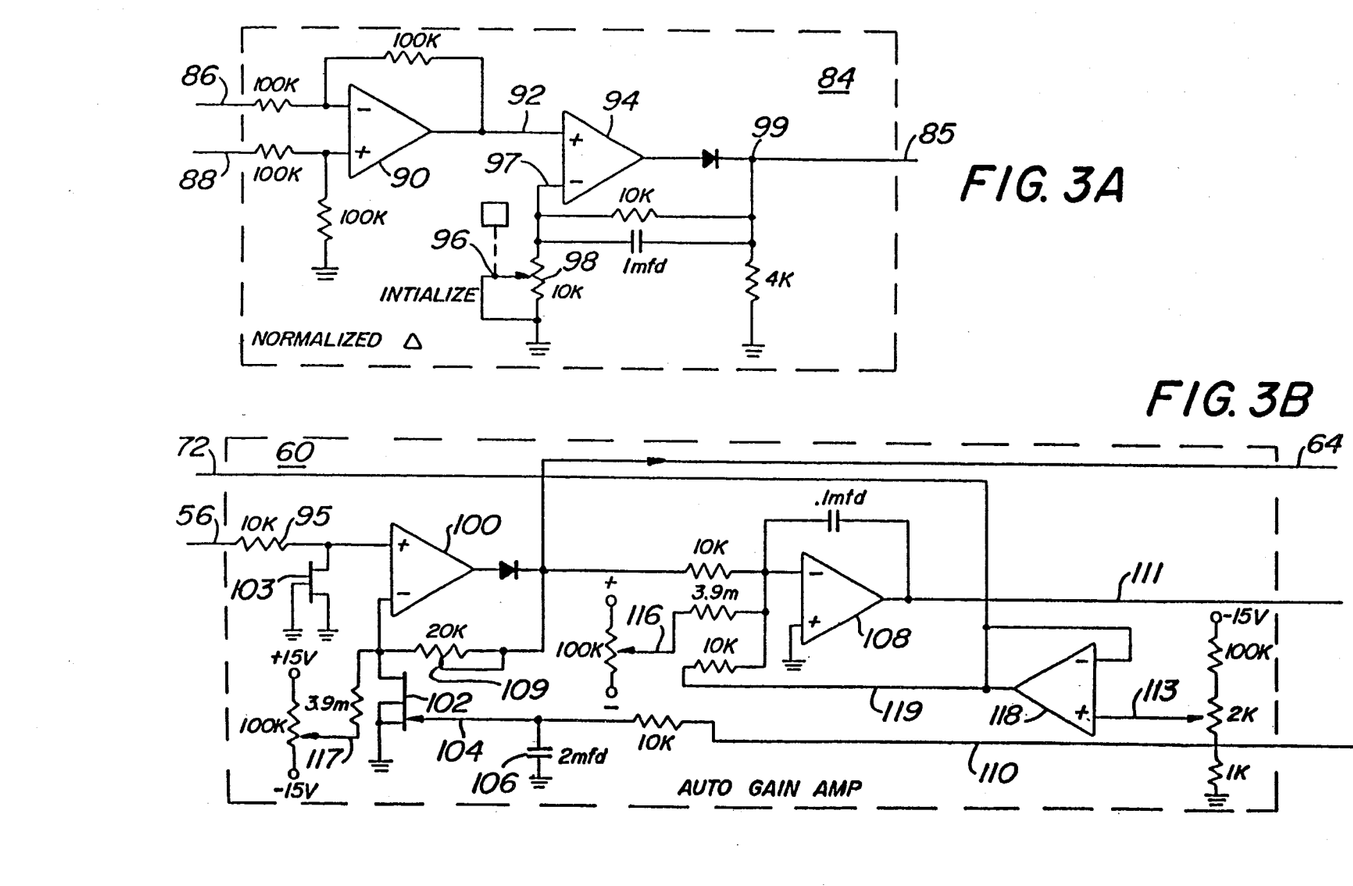
FIG. 3A is a circuit diagram of the normalized Δ circuit.
FIG. 3B is a circuit diagram of the auto gain amplifier circuit.
Figure 3C:
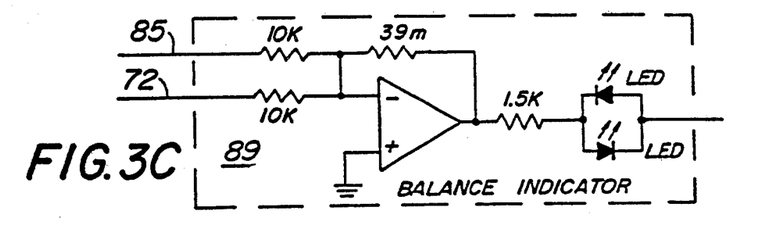
FIG. 3C is a circuit diagram of the balance indicator.

The outputs of sample and hold circuits 80 and 82 are compared in amplifier 90 of normalized $\Delta$ circuit 84 of FIG. 3A so that the difference appears on line 92 as an input to the non-inverting input of amplifier 94. The input to the inverting input of amplifier 94 is adjusted by varying the position of tap 96 on the potentiometer 98 to vary the gain of amplifier 94. This adjustment is made so that the output of amplifier 94 will be a predetermined value after the initial calibration of the cell 10 is made.

In a normal initial calibration cell 10 can be manually calibrated with an air sample before the cell is inserted into the sample to be measured. At the time of the initial calibration with air, the automatic calibrating mode can be utilized to establish an initial value for $\Delta$ for cell 10 on line 85. That value is established by varying the input to line 97 of amplifier 94 by the above mentioned adjustment of tap 96. This initial value for the signal on line 85 must, of course, be within the limits set up for $\Delta$, as detected by the limit indicators 87 and will correspond to the reference value set on tap 113 (FIG. 3B).

The output appearing at line 85 is supplied through switch S3 to an input line 56 of the auto gain amplifier 60, where it appears as one of the inputs to amplifier 100 whose gain is adjusted by the circuitry of the auto gain amplifier 60, as shown in FIG. 3B. For these purposes, the FET 102 is connected to the inverting input of amplifier 100 and FET 102 is biased by a signal on line 104 depending upon the value stored in capacitor 106 as a result of the output from summing amplifier 108 which connects by way of lines 111 and relay RL-1 to the line 110 to establish the voltage across capacitor 106. It should be noted that capacitor 106 must be a very high quality capacitor having minimum leakage so it will maintain its charge over a one hour period between automatic calibrations. The charge on capacitor 106 determines the gain of amplifier 100, the gain being also determined by the position of tap 109 which is adjusted at initial calibration. It will be evident from the circuit of the automatic gain amplifier 60 that the amplifier 108 compares the output of amplifier 100, the manually adjusted offset voltage from potentiometer tap 116, and the output of amplifier 118 so that the output on line 111 is proportional to the concentration of the species being measured.

The gain of amplifier 100 is thus representative of the sensitivity of the cell 10 as is the charge on capacitor 106. Upon a change in the charge from one value to the next as a result of a change in $\Delta$ from $\Delta_1$ to $\Delta_2$, as represented by the signals on line 56, the gain of amplifier 100 changes in accordance with the ratio $\Delta_1/\Delta_2$.

The voltage sources established by the positions for potentiometer taps 116 and 117 provide means for adjusting the inputs to amplifiers 108 and 100, respectively, for any offsets in the amplifiers which need to be compensated.

Figure 5:
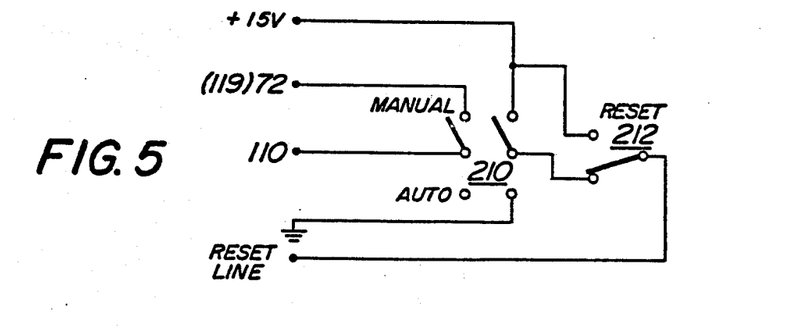
FIG. 5 is a circuit diagram of switch arrangement useful in operating the circuits of this invention.

The initial calibration process is started by adjusting tap 46 with switch 210 (FIG. 5) in the manual position and with the cell in air, for example, so that the indicator 50 shows the appropriate calibration point. Then the switch 210 is placed in the auto position for auto calibration. That switch operation causes a reset signal to be sent to the timing circuits of FIG. 4. This reset signal is also the reset switch 212 (FIG. 5). As a result of that reset signal, the timing circuit 60 puts out the timing signals in FIG. 4. The $\Delta$ timing pulses will then establish a value $\Delta$ on line 92 for the existing condition and for the standard sample being used. After the $\Delta$ timing cycle is complete a gain standardization is carried out. This is accomplished during the period established by the timing identified for initial calibration in FIG. 4. By adjusting tap 96 during initial calibration, the balance indicator 89 of FIG. 3C can be balanced, as will be indicated by the lighting of both LEDs, so that the potential on line 85 is equal to that on line 72. Since the potential on line 72 is set by tap 113 at 0.3 volts, for example, then the potential on line 56 will be 0.3 volts. That voltage will be dropped by the voltage divider formed by resistor 95 and FET 103 at the non-inverting input of amplifier 100 so that the input is lower than 0.3. The potential on line 110 will also be 0.3 volts by virtue of the relay RL-1 being closed to make a connection between lines 111 and 110. Thus, the gain of amplifier 100 will be established by a combination of the voltage on line 104 and the setting of tap 109 with the amplifier 108 adjusting the voltage on line 110 to that value which will make its input from amplifier 100 equal the voltage on line 119 or 0.3 volts.

A second FET 103 is connected in the non-inverting input for amplifier 100 to balance the temperature effect of FET 102.

Figure 3D:
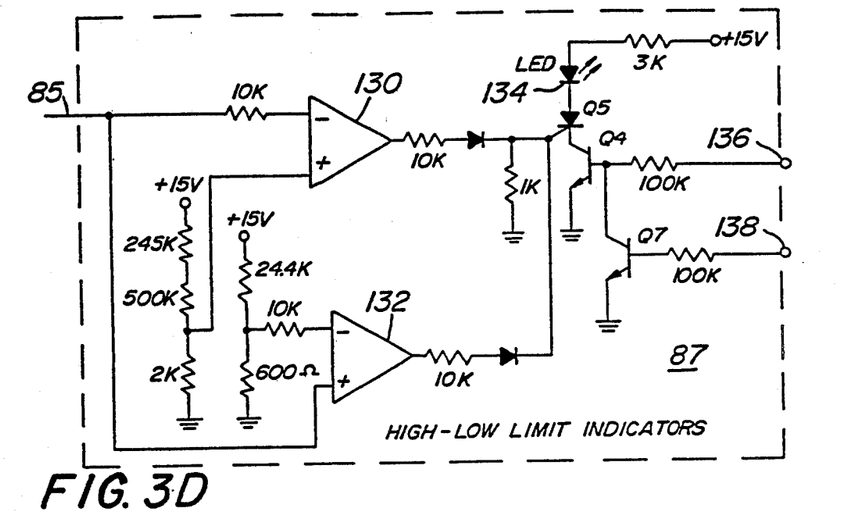
FIG. 3D is a circuit diagram of the high-low limit indicator.

In FIG. 3D a circuit for the high-low limit indicator is shown. This circuit has for its purpose the indication of any out-of-range condition which makes recalibration necessary. Such out-of-range conditions occur because of the limited range which can be accommodated by certain component values. Adjustment of tap 46 and a reinitialization can be utilized to bring the circuit back into range and initialize for the new condition.

The signal representing $\Delta$ which appears on line 85 provides an input to both differential amplifiers 130 and 132. The other inputs to these amplifiers are provided from voltage dividers supplied from a +15 volt source. When the value of $\Delta$ exceeds the values established from the voltage dividers, the diodes in the amplifier outputs allow output current to turn on the SCR Q5 which is connected to ground through transistor Q4, which is in turn turned on and off by Q7, to cause LED 134 to light indicating a limit condition. The on-off states of Q4 and Q7 are controlled by the timing signals introduced at terminals 136 and 138, respectively.

Figure 3E:
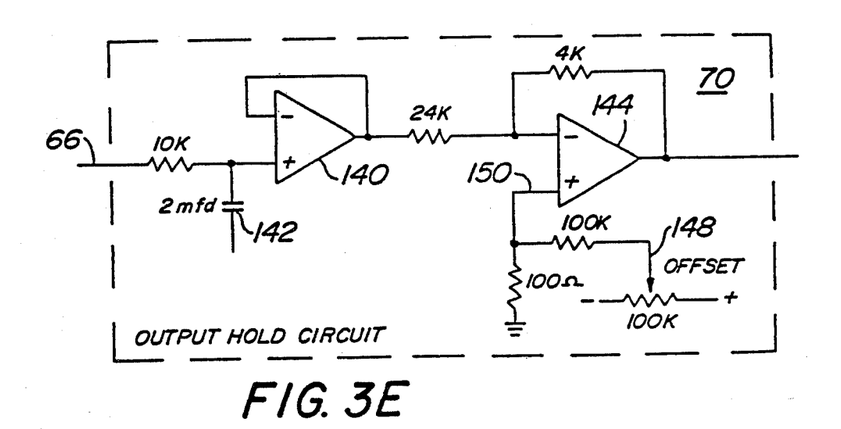
FIG. 3E is a circuit diagram of the output hold circuit.

FIG. 3E shows a circuit which can be used for the output hold circuit 70. That circuit is designed to hold the measured value appearing on line 66 during the calibration period when S5 is open. For this purpose the amplifier 140 is provided with a capacitor 142 to form a sample and hold circuit such as that shown in FIG. 3F. The amplifier 144 serves to invert the signal from amplifier 140 and to provide the addition of an offset compensating voltage as supplied from the potentiometer tap 148 to the input 150 of amplifier 144.

Figure 3F:
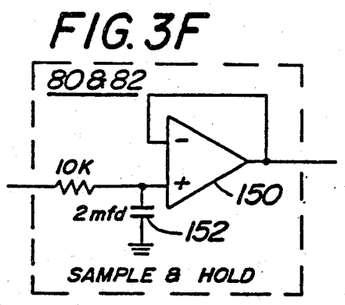
FIG. 3F is a circuit diagram of the sample and hold circuit.

FIG. 3F shows details of a sample and hold circuit such as required for 80 and 82. Amplifier 150 has a capacitor 152 for maintaining the signal on the non-inverting input to hold the output after the input has ceased.

Figure 3G:
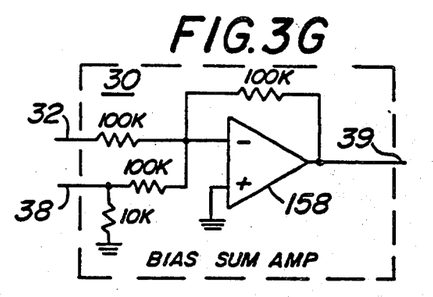
FIG. 3G is a circuit diagram of the bias sum amplifier.

In FIG. 3G a circuit for the bias sum amplifier 30 is shown. That circuit includes the differential amplifier 158 which is connected as a summing amplifier so that the inputs on lines 32 and 38 are summed to produce the output on line 39.

Figures 3H, 3I:
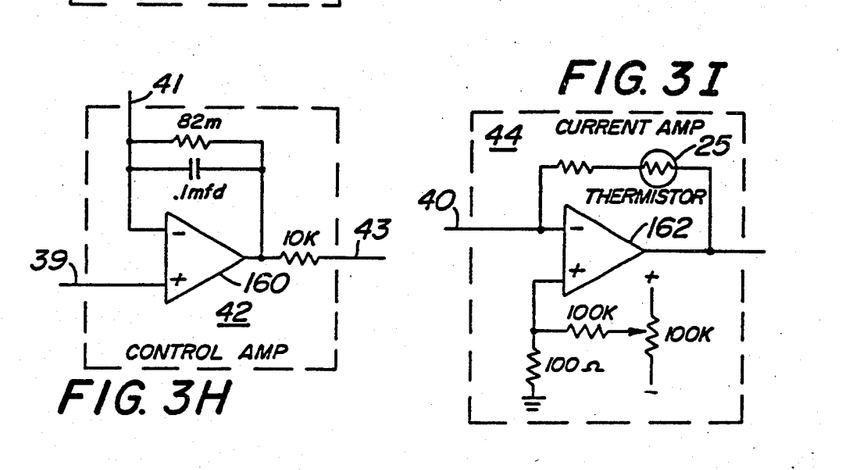
FIG. 3H is a circuit diagram of the control amplifier.
FIG. 3I is a circuit diagram of the current amplifier.

In FIG. 3H a circuit is shown for control amplifier 42. This circuit uses the differential amplifier 160 to control the current output on line 43 so that the potential on the reference electrode as established on line 41 is maintained equal to the potential on line 39 representing the bias desired for the cell.

FIG. 3I shows a circuit for the temperature compensator and current amplifier 44. That circuit includes a differential amplifier 162 which provides an output to calibration potentiometer 48 proportional to the input current from the cathode 14. An adjustable bias or offset circuit is connected to the non-inverting input of amplifier 162 to provide an offset to its output as may be needed for proper measurement with the cell 10. The output of amplifier 162 is modified by its feedback circuit which includes thermistor 25 which provides temperature compensation for cell 10 so that the output of amplifier 162 has the same relation to the concentration of oxygen in the sample being measured regardless of the temperature of that sample. Thermistor 25 is mounted in the cell itself, as shown in FIG. 1.

In carrying out the automatic calibration of the cell 10 a stepwise change in the current to the fourth electrode 26 is made as previously explained. Thus, a three second timing signal to terminal 170, as shown in FIG. 4, causes transistor Q6 to be conductive to pull in RL-3 for the three second interval to provide from current source 174 the d.c. current to the fourth electrode 26.

The switch S6, which is normally closed, responds to a timing signal to terminal 176 which serves to cause that switch to be open for the full 8 seconds of the automatic calibration period, as shown in FIG. 4. In normal operation the voltage from potentiometer tap 146, representing the oxygen concentration being measured by the cell, is fed through the switch S6 to line 178. Thus the same voltage is present on lines 178 and 179 as inputs to the auto IR compensation circuit 180. This circuit is shown in detail in FIG. 3J. The differential amplifier 182 is connected as a voltage follower circuit with a capacitor 184 to maintain the output of amplifier 182 when switch S6 is disconnected. The output of amplifier 182 provides one of the inputs of amplifier 186 with the other input being supplied from line 179. Thus, during the measurement period the two inputs to the amplifier 186 are equal and the output is only the voltage introduced by the offset compensation provided by the potentiometer tap 188.

Figure 3J:
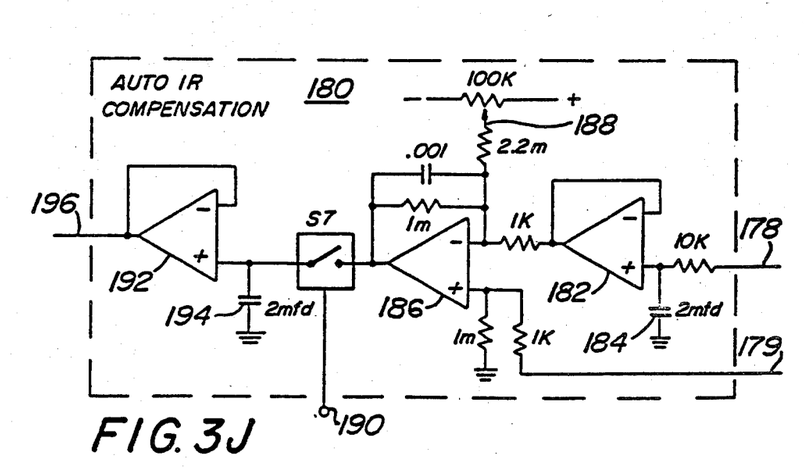
FIG. 3J is a circuit diagram of the auto IR compensation circuit.

The output of amplifier 186 is fed through switch S7 when it is closed by a timing signal on terminal 190. That signal closes S7 for a very short period, such as the 200 millisecond period between $T_0$ and $T_1$ (FIG. 2) which is required for the compensating change in the bias to cell 10 to be completed. The output signal from amplifier 186 which is conducted through the switch S7 to the input of amplifier 192 also charges the capacitor 194 to maintain the input to the amplifier 192 after the switch S7 is opened. Thus for a period of 200 ms the amplifier 186 drives the output on line 196 to maintain equal the output of 182 and the signal on line 179. The output of 192 on line 196 operates through a closed switch S8 to provide a compensating change in the bias for the cell 10 necessary to maintain the cathode current at the value existing when S6 opened.

The charge stored on capacitor 194 maintains the compensating signal on line 38 for the full three seconds of the closure of S8 as determined by the timing signal supplied to terminal 198, as shown in FIG. 4.

From the above it can be seen that the automatic calibration period begins with a pulse that closes RL-3 allowing a calibrating constant current to be introduced into the cell for 3 seconds. At the instant the calibrating current is applied, S6 opens for 8 seconds; S7 and S8 close. With the switches in these positions, amplifier 182 now holds at its output the previous cathode current value, which is then fed to the inverting input of amplifier 186, a high-gain differential amplifier. The non-inverting input of amplifier 186 monitors the cathode current directly. Prior to the calibration period, the output of amplifier 186 was zero volts, assuming no offset, but as the cathode current begins to increase, due to the calibrating current being applied, a difference occurs at the output of amplifier 186. This difference is directed through S7, which closes for 200 milliseconds, to a sample and hold amplifier 192, which monitors the difference for the 200 milliseconds. That difference signal is then delivered to the summing input of amplifier 158 (FIG. 3G) by way of switch S8, which is closed for 3 seconds and that difference will turn out to be the change in the bias needed to cause the cathode current to have the value it had prior to the calibration period.

Thus, during the time that S7 is closed, the cathode current is clamped at the value it was prior to intiating the calibration sequence and when the end of the 200 millisecond pulse allows S7 to open, amplifier 192 holds the summing point of amplifier 158 (FIG. 3G) at the corrected bias voltage until S8 and RL-3 are opened, thus there is made the correction to the bias voltage necessary to compensate for the IR drop in the reference-to-cathode path of the solution being measured by cell 10, so that the IR drop will not cause the cell to operate on a different part of its characteristic, which would disturb the accuracy of the calibration.

With the opening of S8 and RL-3, the bias voltage is returned to its normal present value. Normal measuring operation is then resumed with the closure of switch S6.

Figure 3K:
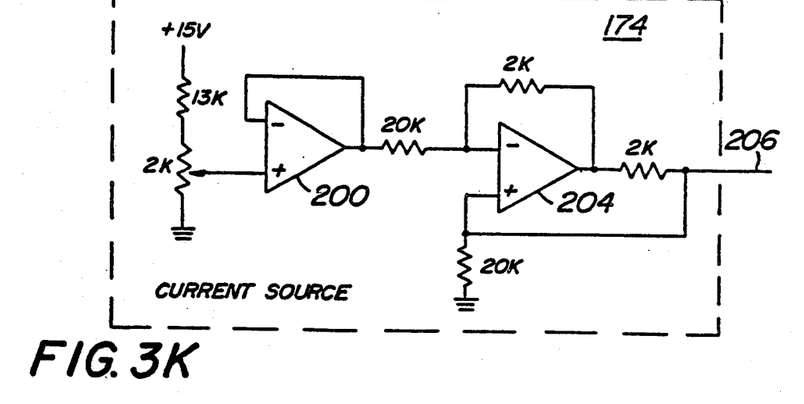
FIG. 3K is a circuit diagram of the current source.

In FIG. 3K there is shown a circuit which can be used for the current source 174. That source may, for example, be capable of delivering 50 microamps to the fourth electrode 26. As shown, the voltage follower formed with amplifier 200 receives its input from potentiometer tap 202 and provides the input to amplifier 204 at its inverting input. Amplifier 204 is connected to supply a current output on line 206 to the fourth electrode for the period of the closure of relay RL-3 with the magnitude of the current being dependent on the setting of tap 202.

FIGS. 4A and 4B show one form of the clock and timing circuits 60 which are required for the circuit of FIG. 3 to provide operation as described above. There are, of course, many other possible forms these timing circuits can take. Thus, FIGS. 4A and 4B are provided only by way of example. The circuits of FIGS. 4A and 4B utilize standard components, as shown, and require no unusual skill in construction.

In FIG. 5 there is shown the manually operated switches necessary for switching the circuits of FIG. 3 and 4 between manual and automatic operation and to reset the timing circuits of FIGS. 4A and 4B. When the manual-auto switch 210 is in its manual position, to avoid automatic calibration procedures the one blade of the switch connects lines 72 and 110 to determine the gain of the auto gain amplifier 60. At the same time the other blade of the switch 210 connects a +15 volt supply to the reset line of the circuits of FIGS. 4A and 4B. This connection is made through the normally closed contacts of the reset switch 212.

When switch 210 is in the auto position, the reset line is connected to ground, unless, of course, the reset switch 212 is in the reset position which directly connects the reset line to the +15 volt supply to reset the timing circuits of FIGS. 4A and 4B.

While there has been described above an analog execution for carrying out this invention, it will be obvious to those of ordinary skill in the art that a digital computer can be utilized advantageously in a system for effecting the automatic calibration with the necessary IR compensation. Such an execution may, for example, calculate the cell sensitivity in accordance with equation (4) set forth above. The calculated cell sensitivity can then be multiplied by the measured cathode current to determine the species concentration in the sample being tested, in accordance with the relationship set forth in equation (1).

In a digital execution, for example, the potential detected at tap 46 can be used as an input to an analog-to-digital converter which can then supply the digital representations for $I_2$ and $I_3$ (FIG. 2) so that $\Delta$ can be calculated as $I_3 - I_2$. The temperature values $T_1$ and $T_2$ would, of course, have to be obtained by measuring the temperature detected by thermistor 25 (FIG. 1) separately. With $\Delta_2$ and $\Delta_2$ calculated and with the quantities $T_1$ and $T_2$ measured, the values of $B_1$ and $B_2$ along with the initial sensitivity value $S_1$ can be utilized with equation (4) to calculate $S_2$. As mentioned, the value of $S_2$, which can be determined every hour can then be multiplied by the cathode current $I_c$ to obtain a digital readout or record of the concentration C of the species being measured. Since the calculation of an equation such as equation (4) is a routine and elementary calculation when carried out by a digital computer, no detailed program is disclosed for that calculation.

Figure 6A:
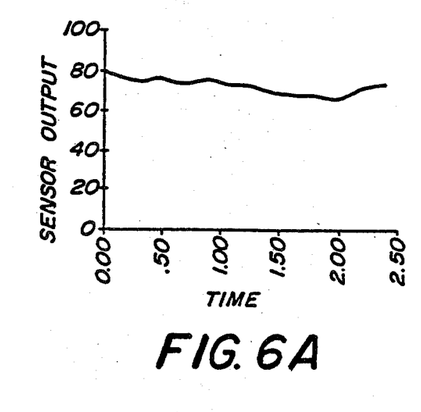
FIG. 6A is a curve showing a drift in sensor output.
Figure 6B:
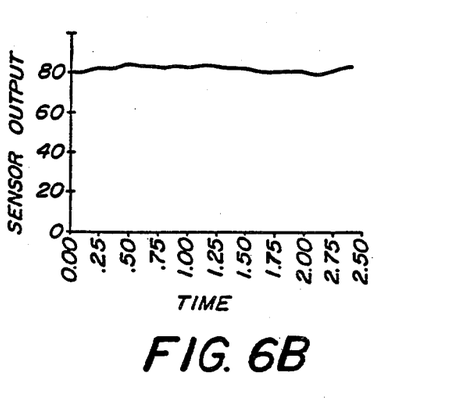
FIG. 6B shows the correction of the drift.

To demonstrate the capability of the present invention, an experiment was carried out under carefully controlled conditions of constant dissolved oxygen concentration during which the output signal of a Ross-type oxygen sensor showed significant variations with time. The curve of FIG. 6A shows the output signal variations, with an overall decrease in sensor output (sensitivity) of approximately 20 percent (20%) during the experiment. Determining this sensitivity change and correcting for this drift by using this invention resulted in the corrected output recorded as the curved of FIG. 6B showing a reduction of the error due to sensor sensitivity changes to a negligible level resulting in an effectively constant output signal appropriate for the constant dissolved oxygen concentration of this experiment.

What is claimed is:

1. In a system for measuring the concentration of an electrochemically active species by measuring the current through a polarographic type cell, wherein means are provided for recalibration of said system by injecting additional current into said cell and measuring the factor by which the cell's transient response to said current injection has changed since the last calibration as an indication of the factor by which the calibration has changed, apparatus for compensating for the IR drop in said cell due to said injected current, comprising:

means operable for a brief initial part of the period of said current injection for changing the cell bias so as to maintain the total cell current for said brief initial part of that period at the value it had just before said current injection, said brief initial part of the period being of duration sufficient for the effect of the IR drop to be compensated by said change in bias but not sufficient to extend into that part of the injection period when electrochemical action due to the injection affects the total cell current; and means for maintaining throughout the remainder of said injection period the cell bias which exists at the end of said brief initial part of said injection period.

2. A method for automatically compensating for IR drops in a polarographic type electrochemical cell caused by additional cell current not required by the measurement being made with the cell comprising the steps of:

adjusting the bias of said cell during a brief initial part of the period when said additional cell current is present so as to maintain the total cell current during said initial part of the period at the value it had just before said additional current, said brief initial part of the period being of duration sufficient for the change in bias to be effected but not sufficient to extend into that part of the period when electrochemical action due to the injection affects the total cell current; and maintaining throughout the remainder of said period the cells bias which exists at the end of said brief part of said period.

3. In a system for measuring the concentration of an electrochemically active species by measuring the current through a polarographic type cell which includes a cathode, an anode, a reference electrode and a fourth electrode, wherein a current amplifier connected to said cathode produces a voltage representing the total cell current, a control amplifier is operable to control the normal electrode current so as to produce a desired bias between said reference electrode and said cathode, a bias summing amplifier produces an input to said control amplifier to establish said desired bias as the sum of a preset bias and a compensating bias, and wherein means are provided for recalibration of said system by injecting additional current into said cell and measuring the factor by which the cell's transient response to said current injection has changed since the last calibration as an indication of the factor by which the calibration has changed; apparatus for automatically adjusting said compensating bias to compensate for the IR drop in said cell due to said injected current, comprising:

a first sample and hold circuit having unity gain and connected to receive as an input said voltage representing the total cell current;

a first switch means operable to automatically disconnect the input to said first sample and hold circuit for the duration of said injection period;

a high gain amplifier for comparing the output of said first sample and hold circuit with the said voltage representing the total cell current;

a second sample and hold circuit;

a second switch means operable to connect the output of said high gain amplifier to the input of said second sample and hold circuit for a brief initial part of each injection period;

a third switch means for connecting the output of said second sample and hold to the bias summing amplifier as said compensating bias so that for said brief initial part of the period of said current injection the compensating cell bias changes so as to maintain the total cell current for said brief initial part of that period at the value it had just before said current injection and for the remainder of said injection period the cell bias which exists at the end of said brief initial part of said injection period is maintained in compensation of said IR drop.

* * * * *